US012629025B2

(12) United States Patent
Alasaarela

(10) Patent No.: US 12,629,025 B2
(45) Date of Patent: May 19, 2026

(54) OPHTHALMIC APPARATUS AND METHOD OF IMAGING RETINA

(71) Applicant: Optomed Plc, Oulu (FI)

(72) Inventor: Ilkka Alasaarela, Oulu (FI)

(73) Assignee: OPTOMED PLC, Oulu (FI)

( * ) Notice: Subject to any disclaimer, the term of this patent is extended or adjusted under 35 U.S.C. 154(b) by 320 days.

(21) Appl. No.: 18/496,173

(22) Filed: Oct. 27, 2023

(65) Prior Publication Data

US 2024/0138674 A1 May 2, 2024

(30) Foreign Application Priority Data

Oct. 28, 2022 (FI) ..................................... 20225964

(51) Int. Cl.
| | |
|---|---|
| *A61B 3/14* | (2006.01) |
| *A61B 3/00* | (2006.01) |
| (Continued) | |

(52) U.S. Cl.
CPC .............. *A61B 3/14* (2013.01); *A61B 3/0025* (2013.01); *A61B 3/12* (2013.01); *A61B 3/152* (2013.01);
(Continued)

(58) Field of Classification Search
CPC ........... A61B 3/14; A61B 3/0025; A61B 3/12; A61B 3/152; A61B 2560/02; A61B 3/00;
(Continued)

(56) References Cited

U.S. PATENT DOCUMENTS

| | | |
|---|---|---|
| 2004/0189942 A1 | 9/2004 | Yoon |
| 2004/0228005 A1 | 11/2004 | Dowski et al. |
| | (Continued) | |

FOREIGN PATENT DOCUMENTS

| | | |
|---|---|---|
| EP | 1321095 A2 | 6/2003 |
| EP | 1 978 394 | 10/2008 |
| | (Continued) | |

OTHER PUBLICATIONS

May 15, 2024 Search Report issued in Finnish U.S. Appl. No. 20/236,197, pp. 1-2.
(Continued)

*Primary Examiner* — Mohammed A Hasan
(74) *Attorney, Agent, or Firm* — Nixon & Vanderhye PC

(57) ABSTRACT

An ophthalmic apparatus comprises an optical arrangement that causes or imitates, for forming at least one image that is in focus, a longitudinal chromatic and/or spherical aberration of an optical spectrum of light, while the retina is configured to locate within a longitudinal aberration range of the aberration in response to a distance between the ophthalmic apparatus and the eye being within a working range of the ophthalmic apparatus. An image capturing arrangement captures one or more images of the retina through the imaging channel while the distance between the ophthalmic apparatus and the eye is within a working range of the ophthalmic apparatus. A filter filters at least one image from the one or more images of the retina that is in focus for further processing in a data processing unit of the ophthalmic apparatus.

15 Claims, 2 Drawing Sheets

Figure 1:
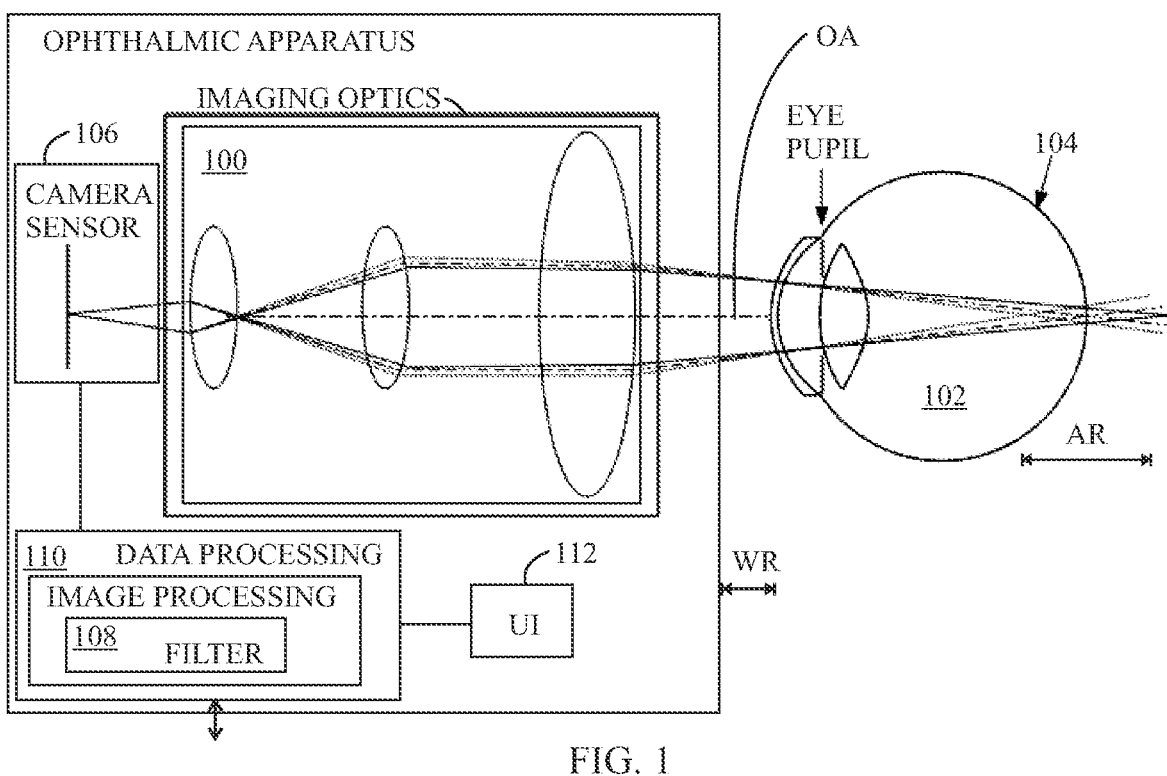

(51) Int. Cl.

| | | |
|---|---|---|
| *A61B 3/12* | (2006.01) |
| *A61B 3/15* | (2006.01) |
| *G06T 7/00* | (2017.01) |

(52) U.S. Cl.
　CPC ........ *G06T 7/0012* (2013.01); *A61B 2560/02* (2013.01); *G06T 2207/30041* (2013.01)

(58) Field of Classification Search
　CPC ................... A61B 3/13; G06T 7/0012; G06T 2207/30041; G06T 2207/10024; G06T 5/73; G02B 27/0025; G02B 27/0075
　USPC ......................................................... 351/206
　See application file for complete search history.

(56) References Cited

U.S. PATENT DOCUMENTS

| | | | |
|---|---|---|---|
| 2005/0225725 | A1 | 10/2005 | Warden et al. |
| 2011/0242372 | A1 | 10/2011 | Kosaka |
| 2015/0055358 | A1* | 2/2015 | Nitta .................... F21S 41/321 |
| | | | 252/301.4 F |
| 2015/0070655 | A1 | 3/2015 | Rossi |
| 2018/0055358 | A1 | 3/2018 | Nakajima |
| 2018/0136486 | A1* | 5/2018 | Macnamara ............. A61B 3/00 |
| 2020/0054211 | A1* | 2/2020 | Ohmura ................. A61B 3/102 |
| 2020/0054212 | A1* | 2/2020 | Ohmura .................. A61B 3/13 |
| 2022/0057651 | A1 | 2/2022 | Segre et al. |
| 2022/0386868 | A1* | 12/2022 | Ono .......................... A61B 3/12 |
| 2023/0248238 | A1* | 8/2023 | Lipponen ................. A61B 3/14 |
| | | | 351/208 |
| 2023/0359008 | A1 | 11/2023 | Shimizu et al. |
| 2023/0404402 | A1* | 12/2023 | Alasaarela ............... A61B 3/12 |

FOREIGN PATENT DOCUMENTS

| | | | | |
|---|---|---|---|---|
| EP | 1978394 | A1 * | 10/2008 | ......... G02B 27/0075 |
| EP | 2 786 699 | | 10/2014 | |
| WO | 96/41123 | | 12/1996 | |
| WO | 2008000008 | A2 | 1/2008 | |
| WO | 2018152596 | A1 | 8/2018 | |
| WO | 2020010138 | A1 | 1/2020 | |
| WO | 2020/231894 | | 11/2020 | |
| WO | 2022/011420 | | 1/2022 | |

OTHER PUBLICATIONS

May 15, 2024 Office Action issued in Finnish Patent Application No. 20236197, pp. 1-5.

Finland Search Report for FI20225964 dated May 11, 2023, 4 pages.

May 29, 2024 Office Action issued in Finnish U.S. Appl. No. 20/236,198, pp. 1-7.

* cited by examiner

OPHTHALMIC APPARATUS AND METHOD OF IMAGING RETINA

CROSS-REFERENCE TO RELATED APPLICATION

This application claims priority to FI 20225964 filed Oct. 28, 2022, the entire contents of which are hereby incorporated by reference.

FIELD

The invention relates to an ophthalmic apparatus and a method of imaging retina.

BACKGROUND

Capturing sharp and reflection free images from the retina of a patient under examination of an eye is challenging due to movement of patient and patient's eye, eye refractive errors such as myopia or hyperopia, and eye accommodation, which may quickly change both the alignment and the focus as a function of time, for example. Additionally, fundus imaging is challenging and good quality images to resolve maximum number of details from retina are hard to capture. Hence, a new approach to the eye examination would be welcome.

BRIEF DESCRIPTION

The present invention seeks to provide an improvement in the ophthalmic examination.

The invention is defined by the independent claims. Embodiments are defined in the dependent claims.

If one or more of the embodiments is considered not to fall under the scope of the independent claims, such an embodiment is or such embodiments are still useful for understanding features of the invention.

LIST OF DRAWINGS

Figure 2:
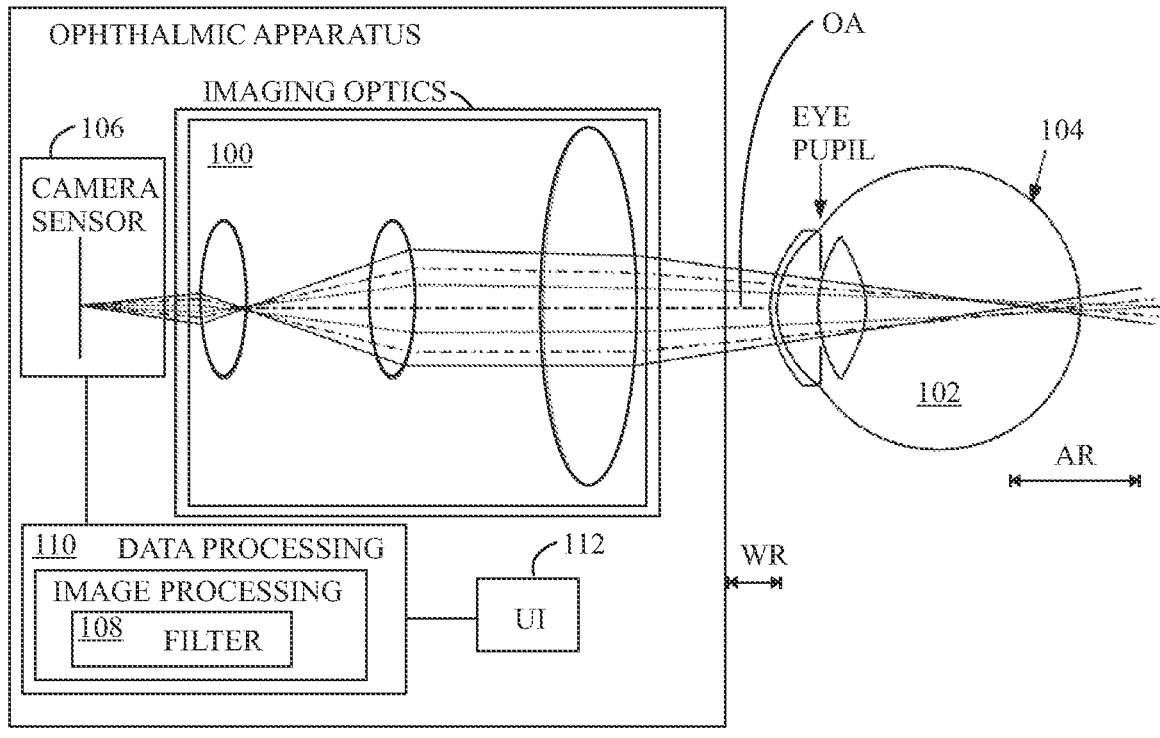
Figure 3:
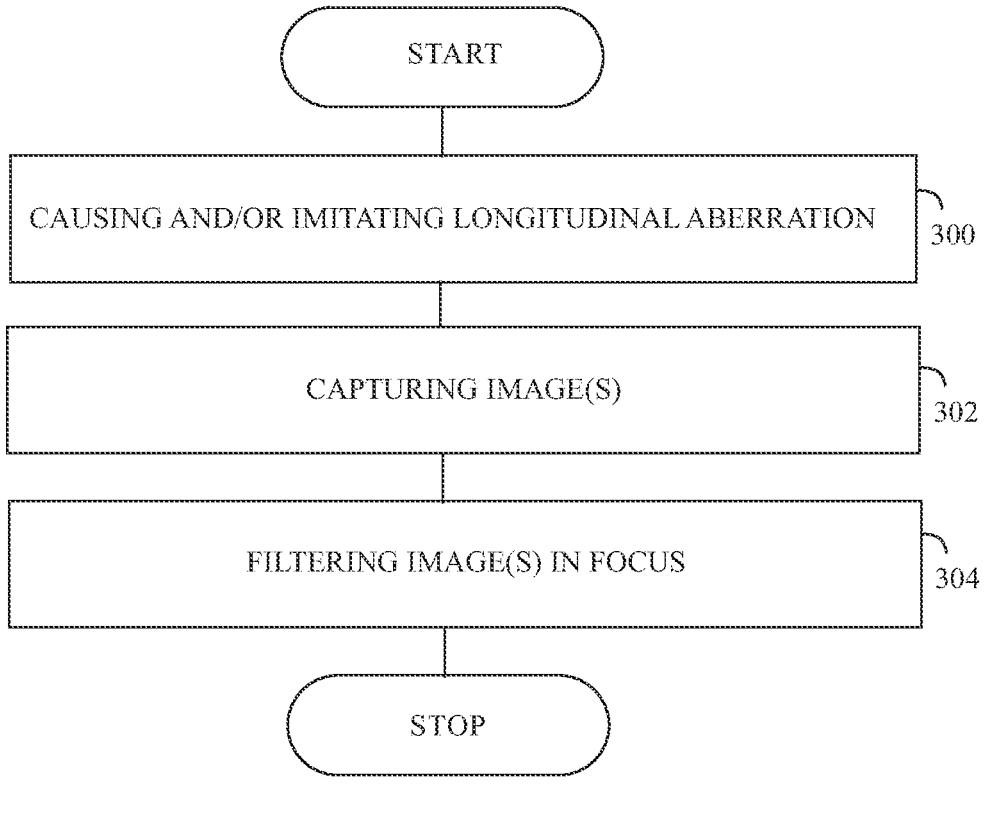

Example embodiments of the present invention are described below, by way of example only, with reference to the accompanying drawings, in which FIG. 1 illustrates an example of ray paths originating from one point on the fundus camera sensor are focused to different distances from the retina by different wavelength bands;

FIG. 2 illustrates an example of ray paths originating from three points on the fundus camera sensor are focused to different distances from the retina by different pupil zones; and FIG. 3 illustrate an example of flow chart of imaging of retina.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment.

The articles "a" and "an" give a general sense of entities, structures, components, compositions, operations, functions, connections or the like in this document. Note also that singular terms may include pluralities.

Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

The term "about" means that quantities or any numeric values are not exact and typically need not be exact. The reason may be tolerance, resolution, measurement error, rounding off or the like, or a fact that the feature of the solution in this document only requires that the quantity or numeric value is approximately that large. A certain tolerance is always included in real life quantities and numeric values.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

The term "comprise" (and grammatical variations thereof) and the term "include" should be read as "comprise without limitation" and "include without limitation", respectively.

"Lens" means a single lens, compound lens or set of lenses. For example, an achromatic doublet is a lens.

In this document, the standard eye may be based on an Emsley model, Emsley-Gullstrand model, or Liou and Brennan schematic eye model, for example. The eye model may be similar to an anatomical and optical eye. It may have a power of about 60.4 D and an axial length of about 24 mm for example. The eye model may estimate aberrations in a visible range of light. The eye model used in the the ophthalmic examination apparatus during an examination may have variation depending on a size of a person that is examined, sex and age especially when it is a question of a child, for example. That is, a model may be selected based on anatomical and/or optical information on the person or animal to be examined.

In this document, the sharpness of the image, can be judged by terms of modulation transfer function (MTF), RMS spot diameter, or wavefront error for example. When using MTF, for example, a MTF criteria may be set, which states that MTF needs to be above certain threshold at certain spatial frequency, in order to image to be "sharp". The threshold may be for example 10%, or 20%, and the frequency may be for example the Nyquist frequency of the camera sensor, or half of the Nyquist frequency for example. The MTF criteria may also be set by the standard requirements, such as fundus camera standards. If the image sharpness fulfils the standard requirements, the image may be called "sharp". In general, "sharp" image means that it fulfils the requirements for the image sharpness. This means, small enough details can be distinguished for the desired purpose. In other words, the resolution of the image is suitable for the examination.

In typical fundus camera, retina is imaged to a camera sensor, and the optics is designed so that the retinal image on the sensor will be sharp. Opposite to that, in this description a fundus camera is described, which forms purposefully unsharp image of the retina to the camera sensor, in order to form sharp image by the help of digital filtering. By that way, larger depth-of-field can be achieved than with conventional fundus cameras. Larger depth-of-view brings advantages such as better usability and better image quality in the fundus imaging.

In conventional fundus imaging, in order to achieve sharp image, image aberrations such as longitudinal chromatic aberration and spherical aberrations needs to be minimized. In the method and system described in this document at least one of these two aberrations are not minimized, but made purposefully larger so that the retinal image on the sensor becomes unsharp, but such a way, that by digital filtering, a sharp image of the retina can still be formed from larger depth-of-field than what is possible by the conventional fundus imaging.

In this document, when referring to a wavelength, instead of monochromatic wavelength it may mean a wavelength range centered to a certain wavelength. For example, red, green, and blue wavelength bands, used in color CMOS sensors, may be called "wavelengths", even they may have bandwidths of tens of nanometers. FIGS. 1 and 2 illustrate examples of an ophthalmic apparatus 10 that comprises an optical arrangement 100 that causes purposefully, for forming at least one image that is in focus, a longitudinal chromatic and/or spherical aberration of an optical spectrum of light received through an imaging channel of the ophthalmic apparatus from the retina 104 by the ophthalmic apparatus. The optical spectrum of light is directed through an illumination channel of the ophthalmic apparatus to the retina 104 of the eye 102. The retina 104 should then be located within a longitudinal aberration range AR of the aberration in response to a distance D1 between the ophthalmic apparatus and the eye 102 being within a working range (WR) of the ophthalmic apparatus.

In an embodiment, the light may be directed through an illumination channel of the ophthalmic apparatus to a retina 104 of an eye 102 and/or received through an imaging channel of the ophthalmic apparatus from the retina 104, while the retina 104 is located within a longitudinal aberration range AR of the aberration in response to a distance D1 between the ophthalmic apparatus and the eye 102 being within a working range (WR) of the ophthalmic apparatus. The imaging channel may cause purposefully, for forming at least one image that is in focus, a spherical aberration and/or a longitudinal chromatic aberration when imaging the retina 104 of an eye 102 to the detection performed in the ophthalmic apparatus.

The illumination channel refers to a path of light through which the light from a light source travels to the retina 104. The illumination channel includes, or the light traveling within the illumination path is affected by optical components which may comprise lenses and/or mirrors, for example.

The imaging channel refers to a path of light through which the light from the retina 104 travels to detection performed in the ophthalmic apparatus. The imaging channel includes, or the light travelling within the optical channel is affected by, optical components, which may comprise lenses and/or mirrors, for example. The light directed to the eye 102 through the illumination channel and/or the light received through the imaging channel may include infrared light and/or visible light. The light directed to the eye 102 through the illumination channel and/or the light received through the imaging channel may include only infrared light and/or only visible light.

The infrared light may comprise light with wavelengths ranging from about 700 nm to about 1200 nm, for example, or ranging from about 800 nm to about 1000 nm for example. The visible light may comprise light with wavelengths ranging from about 370 nm to about 800 nm for example, or ranging from about 400 nm to about 700 nm, for example.

Fundus camera may have field-of-view more than 20 deg for example, or more than 40 deg for example.

Instead of causing or in addition to causing the longitudinal chromatic and/or spherical aberration, the optical arrangement 100 may imitate the longitudinal chromatic and/or spherical aberration by directing beams or rays of light on the retina 104 in a manner corresponding to the chromatic and/or spherical aberration. When imitating the chromatic aberration beams or rays of light of different wavelength are made to focus at different points along the optical axis. When imitating the spherical aberration beams or rays of light regardless their wavelengths are made to focus at different points along the optical axis OA. The spherical aberration may be imitated by making the focusing point of the beams or rays of light to be a function of the radial distance of a location at which they are directed toward the retina 104 from the optical axis OA. A person skilled in the art knows chromatic and spherical aberration, per se. Note that in optics the explanation of the optical operation does not necessarily refer to the actual propagation direction of light. That means, light may in reality travel either in the same direction as described in the explanation or in the opposite direction to that of the explanation describing the optical operation based on rays or beams.

The ophthalmic apparatus comprises an image capturing arrangement 106 that captures one or more images of the retina 104 through the imaging channel while the distance between the ophthalmic apparatus and the eye 102 is within a working range WR of the ophthalmic apparatus. The image capturing arrangement 106 may comprise a digital camera, for example. The image capturing arrangement 106 may comprise a CCD (charge-coupled device) and/or CMOS (complementary metal-oxide-semiconductor) camera, for example.

The ophthalmic apparatus comprises a filter 108 that filters at least one image from the one or more images of the retina 104, the at least one image being in the best or optimal focus in each location. Here the best or optimal focus refers to the definition of the sharpness relating to the modulation transfer function (MTF), RMS spot diameter, or wavefront error explained earlier in this document. The filter 108 may be realized as a computer program of image filtering based on digital image processing. The filter 108 may be an application in the image processing of the data processing unit 110 of the ophthalmic apparatus. The data processing unit 110 may be considered a computer. The application may include one or more computer programs of image processing, and the application may comprise a set of instructions that cause the image processing to execute the filtering operation. The filtered image may then be forwarded for further processing in or from the data processing unit 110 of the ophthalmic apparatus. The data processing unit 110 may comprise or be connected with a user interface 112.

In an embodiment, the filter 108 may emphasize the one or more images of the retina 104 based on rays of light that are in-focus as a result of the longitudinal chromatic and/or spherical aberration over the one or more images that are out-of-focus caused by the longitudinal chromatic and/or spherical aberration.

The image may be forwarded in wired manner or a wireless manner from the ophthalmic apparatus to a laptop computer, a tablet computer, a personal computer, a mainframe computer, data network and/or a cloud.

In an embodiment, the filter 108 may perform noise reduction to the at least one image for emphasizing the one or more images in-focus over the one or more images out-of-focus. The noise reduction may treat the one or more images out-of-focus as noise. The blur of the total image including images both out-of-focus and in-focus may be reduced as the blur is treated as noise, which processed with noise reduction.

In an embodiment, the filter 108 comprises a temporal filter that may vary focal plane position of the imaging channel as function of time, and the image capturing arrangement 106 may capture the at least one image synchronously with the varying focal plane position for capturing the at least one image of the retina 104 in-focus. Note that the focal plane is a technical term in optics, and in reality, the focal plane may be planar or curved. In this manner, an in-focus image of the retina 104 can be captured and blurred images can be avoided.

In an embodiment, the temporal filter that may vary focal plane position of the imaging channel as function of time, and the image capturing arrangement 106 may capture a plurality of images each in-focus at different focal plane positions. Then the image processing of the data processing unit 110 may combine into one image the plurality of images covering a full or partial range of the longitudinal aberration range AR. If a full or partial range of the longitudinal aberration range AR is utilized may depend on the variation of the focal plane position. In an embodiment, the noise reduction may be utilized with the varying focal plane position. In an embodiment, if the varying focal plane position cannot cause in-focus images, one or more blurred images may be treated with the noise reduction.

In these manners, a signal-to-noise ratio of the image of the retina 104 may be increased and sharpness and/or resolution of the image of the retina may be increased and more details in the image may become recognizable by human eyes and/or for computational algorithms such as artificial intelligence (AI) and or machine vision (MV). As a result, technical quality of the image may become higher.

A focusing mechanism of the ophthalmic apparatus such as a fundus camera can be implemented for example by a motorized lens barrel, or alternatively by using an electrically tunable liquid lens. The optics which forms the image of the fundus to the sensor may contain a lens, whose focal length is electrically tunable. The focal length adjustment can be used to focus the image to the sensor. By using the liquid lens, mechanical moving parts are avoided.

In addition to that, the depth of focus can be increased and/or focusing range may be extended, by methods described below:

Focus may be spread axially as a function of wavelength or a function of the pupil:

1. When the focus is spread axially as a function of wavelength, axial color aberration is purposefully introduced in the imaging optics, so that the different wavelengths are focused to bit different focus positions. By that way, there is always one or more wavelengths in the best or optimal focus providing spatial information from the finest structures.

Note that as the wavelengths are focused to different focus positions, the image of the retina formed on the camera sensor is not sharp as a whole as every position on the image is combination of in-focus image at certain wavelength, and out-of-focus images at other wavelengths. The same wavelength is not necessarily in-focus over the whole image area, but the wavelength of the sharpest image may vary across the image area.

For example, the fundus camera may comprise a color sensor with red, green, and blue channels. For example, an area of the sensor may capture the best or optimally focused image by blue channel. In that case, the filter may form the brightness modulation to that particular area of the resulting image by using the blue channel brightness modulation, and use information from all color channels for setting the color information to that particular area. By that way, the resulting image may be as sharp as the sharpest image of all three color channels at each image position.

Due to the axial focus aberration, from each position on the sensor, each wavelength is focused to different distances relating to the retina. When the fundus camera is focused to the retina, the retina may be in focus for some wavelength, but for the other wavelengths, retina may be out-of-focus. The maximum difference of the focus distances on the retina between the different wavelengths, may be for example between about 0.1 mm and about 3 mm, or for example between about 0.2 mm and about 1.5 mm, or for example between about 0.3 mm and about 0.5 mm.

2. When the focus is spread as a function of pupil, the light passing the pupil of the imaging lens through different position are focused to bit different focus positions. This can be done for example by introducing purposefully spherical aberration in the imaging optics, so that the different pupil zones, or the different areas of the pupil, have bit different focus. By that way, there is always one or more pupil area in focus providing spatial information from the finest structures.

Examples of the focus spreads 1 and 2 are depicted in FIGS. 1 and 2, respectively. Both of FIGS. 1 and 2 present the imaging channel of a fundus camera with rays between the retina 104 and the camera sensor 106.

Due to the spherical aberration, from each position on the sensor, each pupil zone or pupil area is focused to different distances relating to the retina. When the fundus camera is focused to the retina, the retina may be in focus for some pupil area, but for the other pupil areas, retina may be out-of-focus. The maximum difference of the focus distances on the retina between the different pupil areas, may be for example between about 0.1 mm and about 3 mm, or for example between about 0.2 mm and about 1.5 mm, or for example between about 0.3 and about 0.5 mm.

FIG. 1 shows an example how ray paths originating from one point on the fundus camera sensor 106 are focused to different distances from the retina 104 by different wavelength bands. That may be implemented by selecting the glass materials in the imaging optics purposefully so that longitudinal color aberration is increased to spread the focus surface spectrally in axial direction.

FIG. 2 shows an example how ray paths originating from three points on the fundus camera sensor 106 are focused to different distances from the retina 104 by different pupil zones. This may be implemented by introducing purposefully spherical aberration in the imaging optics, and/or by selecting surface curvatures so that desired axial spread is achieved as a function of pupil zone. In order to achieve that, the imaging optics may comprise both spherical and aspherical surfaces, as well as diffractive optical elements.

By using what is taught of the focus spreads 1 and 2, a depth-of-focus can be extended without moving parts.

Focus may be spread axially as a function of time, i.e., camera may take images from different focus positions in a suitably rapid succession by using a focusing mechanism. The focusing mechanism may contain a motor, which shifts the focus by moving the imaging lens or part of it, or by moving the sensor for example. Instead of moving lens elements or sensor, the lens may contain image deflecting element, such as mirror, prism, or plate, whose movement or rotation can be used to shift the focus, too. The lens may contain one or more electrically tunable liquid lenses, for example. This time-division focus spread may enable good image quality without compromises in color content and/or in image sharpness.

The data processing unit 110 with image processing processes images of the fundus of the eye 102. The user interface 112 may be utilized to show the images. The image information produced by the ophthalmic apparatus may be video or still images. The data processing unit 110 may also control and/or may be used to control operations of the ophthalmic apparatus. The user may also input data and/or commands to the ophthalmic apparatus.

FIG. 3 illustrates an example of a flow chart of a method of imaging retina. In step 300, causing or imitating purposefully a longitudinal chromatic and/or spherical aberration of an optical spectrum of light, for forming at least one image that is in focus, while the retina 104 is configured to locate within a longitudinal aberration range AR of the aberration in response to a distance between the ophthalmic apparatus and the eye 102 being within a working range WR of the ophthalmic apparatus.

In step 302, one or more images of the retina 104 are captured by an image capturing arrangement of the ophthalmic apparatus through the imaging channel, while the distance between the ophthalmic apparatus and the eye 102 is within a working range WR of the ophthalmic apparatus.

In step 304, at least one image from the one or more images of the retina 104 that is in focus is filtered by a filter 108 for further processing in a data processing unit 110 of the ophthalmic apparatus.

In this document and related to the data processing unit 110 and the image processing, the term "computer" includes a computational device that performs logical and arithmetic operations. For example, a "computer" may comprise an electronic computational device, such as an integrated circuit, a microprocessor, a mobile computing device. A "computer" may comprise a central processing unit, an ALU (arithmetic logic unit), a memory unit, and a control unit that controls actions of other components of the computer so that steps of a computer program are executed in a desired sequence. A "computer" may also include at least one peripheral unit that may include an auxiliary memory (such as a disk drive or flash memory), and/or may include data processing circuitry.

The user interface 112 means an input/output device and/or unit. Non-limiting examples of a user interface include a touch screen, other electronic display screen, keyboard, mouse, microphone, display screen, speaker, and/or projector for projecting a visual display.

In this document, illumination and imaging of the retina 104 may be understood to mean in general illumination and imaging of the fundus of the eye 102.

The needed axial chromatic aberration for the imaging channel can be arranged for example by using lenses whose glass materials are selected to have suitable dispersion properties. Alternatively or additionally, combination of prisms or gratings can be used. The needed spherical aberration for the imaging channel can be arranged for example by using lenses with suitable radius of curvature, or for example by using aspherical lenses.

It will be obvious to a person skilled in the art that, as technology advances, the inventive concept can be implemented in various ways. The invention and its embodiments are not limited to the example embodiments described above but may vary within the scope of the claims.

What is claimed is:

1. An ophthalmic apparatus, wherein the ophthalmic apparatus comprises
   an optical arrangement configured to cause and/or imitate, for forming at least one image that is in focus, a spherical aberration and/or a longitudinal chromatic aberration of an optical spectrum of light received through an imaging channel of the ophthalmic apparatus from the retina by the ophthalmic apparatus while the retina is configured to locate within a longitudinal aberration range of the aberration in response to a distance between the ophthalmic apparatus and the eye being within a working range of the ophthalmic apparatus;
   an image capturing arrangement configured to capture one or more images of the retina through the imaging channel while the distance between the ophthalmic apparatus and the eye is within a working range of the ophthalmic apparatus; and
   a filter configured to filter at least one image from the one or more images of the retina that is in focus for further processing in a data processing unit of the ophthalmic apparatus;
   wherein the data processing unit comprises the filter as a computer program of image filtering based on digital image processing, the filter being configured to emphasize the one or more images of the retina based on rays of light that are in-focus as a result of the longitudinal chromatic and/or spherical aberration over the one or more images that are out-of-focus caused by the longitudinal chromatic and/or spherical aberration; and
   wherein the filter is configured to perform noise reduction to the at least one image for emphasizing the one or more images in-focus over the one or more images out-of-focus, the noise reduction being configured to treat the one or more images out-of-focus as noise.

2. The apparatus of claim 1, wherein the image capturing arrangement is configured to capture the at least one image synchronously with a varying focal plane position for capturing the at least one image of the retina in focus.

3. The apparatus of claim 1, wherein the optical spectrum of light is directed through an illumination channel of the ophthalmic apparatus to the retina of the eye.

4. The apparatus of claim 1, wherein the imaging channel is configured to cause the longitudinal chromatic and/or spherical aberration.

5. The method of claim 1, further comprising causing the longitudinal chromatic and/or spherical aberration by the imaging channel.

6. An ophthalmic apparatus, wherein the ophthalmic apparatus comprises
   an optical arrangement configured to cause and/or imitate, for forming at least one image that is in focus, a spherical aberration and/or a longitudinal chromatic aberration of an optical spectrum of light received through an imaging channel of the ophthalmic apparatus from the retina by the ophthalmic apparatus while the retina is configured to locate within a longitudinal aberration range of the aberration in response to a distance between the ophthalmic apparatus and the eye being within a working range of the ophthalmic apparatus;

an image capturing arrangement configured to capture one or more images of the retina through the imaging channel while the distance between the ophthalmic apparatus and the eye is within a working range of the ophthalmic apparatus; and a filter configured to filter at least one image from the one or more images of the retina that is in focus for further processing in a data processing unit of the ophthalmic apparatus;

wherein the filter comprises a temporal filter configured to vary focal plane position of the imaging channel as function of time and the image capturing arrangement is configured to capture a plurality of images each in-focus at different focal plane positions, and the data processing unit is configured to combine into one image the plurality of images covering the longitudinal aberration range fully or partly depending on the variation of the focal plane position.

7. The apparatus of claim 6, wherein the image capturing arrangement is configured to capture the plurality of images synchronously with the varying focal plane position.

8. The apparatus of claim 6, wherein the optical spectrum of light is directed through an illumination channel of the ophthalmic apparatus to the retina of the eye.

9. The apparatus of claim 6, wherein the imaging channel is configured to cause the longitudinal chromatic and/or spherical aberration.

10. A method of imaging retina, the method comprising causing and/or imitating purposefully a longitudinal chromatic and/or spherical aberration of an optical spectrum of light received through an imaging channel of the ophthalmic apparatus from the for forming at least one image that is in focus, while the retina is configured to locate within a longitudinal aberration range of the aberration in response to a distance between the ophthalmic apparatus and the eye being within a working range of the ophthalmic apparatus;

capturing one or more images of the retina through the imaging channel, by an image capturing arrangement of the ophthalmic apparatus, while the distance between the ophthalmic apparatus and the eye is within a working range of the ophthalmic apparatus; and filtering, by a filter, at least one image from the one or more images of the retina that is in focus for further processing in a data processing unit of the ophthalmic apparatus;

wherein the data processing unit comprises the filter as a computer program of image filtering based on digital image processing, the filter being configured to emphasize the one or more images of the retina based on rays of light that are in-focus as a result of the longitudinal chromatic and/or spherical aberration over the one or more images that are out-of-focus caused by the longitudinal chromatic and/or spherical aberration; and wherein the filter is configured to perform noise reduction to the at least one image for emphasizing the one or more images in-focus over the one or more images out-of-focus, the noise reduction being configured to treat the one or more images out-of-focus as noise.

11. The method of claim 10, further comprising directing the optical spectrum of light through an illumination channel of the ophthalmic apparatus to the retina of the eye.

12. A method of imaging retina, the method comprising causing and/or imitating purposefully a longitudinal chromatic and/or spherical aberration of an optical spectrum of light received through an imaging channel of the ophthalmic apparatus from the for forming at least one image that is in focus, while the retina is configured to locate within a longitudinal aberration range of the aberration in response to a distance between the ophthalmic apparatus and the eye being within a working range of the ophthalmic apparatus;

capturing one or more images of the retina through the imaging channel, by an image capturing arrangement of the ophthalmic apparatus, while the distance between the ophthalmic apparatus and the eye is within a working range of the ophthalmic apparatus; and filtering, by a filter, at least one image from the one or more images of the retina that is in focus for further processing in a data processing unit of the ophthalmic apparatus;

wherein the filter comprises a temporal filter configured to vary focal plane position of the imaging channel as function of time and the image capturing arrangement is configured to capture a plurality of images each in-focus at different focal plane positions, and the data processing unit is configured to combine into one image the plurality of images covering the longitudinal aberration range fully or partly depending on the variation of the focal plane position.

13. The method of claim 12, further comprising capturing the plurality of images synchronously with the varying focal plane position.

14. The apparatus of claim 12, further comprising directing the optical spectrum of light through an illumination channel of the ophthalmic apparatus to the retina of the eye.

15. The apparatus of claim 12, further comprising causing the longitudinal chromatic and/or spherical aberration by the imaging channel.

* * * * *